US011922632B2

(12) United States Patent
Chen et al.

(10) Patent No.: US 11,922,632 B2
(45) Date of Patent: Mar. 5, 2024

(54) HUMAN FACE DATA PROCESSING METHOD AND DEVICE, AND COMPUTER-READABLE STORAGE MEDIUM

(71) Applicant: BEIJING GMINE VISION TECHNOLOGIES LTD., Beijing (CN)

(72) Inventors: Wei Chen, Beijing (CN); Boyang Wu, Beijing (CN)

(73) Assignee: BEIJING GMINE VISION TECHNOLOGIES LTD., Beijing (CN)

(*) Notice: Subject to any disclaimer, the term of this patent is extended or adjusted under 35 U.S.C. 154(b) by 59 days.

(21) Appl. No.: 17/773,918

(22) PCT Filed: Nov. 4, 2020

(86) PCT No.: PCT/CN2020/126487
§ 371 (c)(1),
(2) Date: May 3, 2022

(87) PCT Pub. No.: WO2021/088867
PCT Pub. Date: May 14, 2021

(65) Prior Publication Data
US 2022/0392015 A1    Dec. 8, 2022

(30) Foreign Application Priority Data

Nov. 5, 2019  (CN) .......................... 201911068702.2
Dec. 26, 2019  (CN) .......................... 201911361346.3

(51) Int. Cl.
*G06T 7/12*  (2017.01)
*G01R 33/48*  (2006.01)
(Continued)

(52) U.S. Cl.
CPC ................ *G06T 7/12* (2017.01); *G01R 33/48* (2013.01); *G06T 3/0012* (2013.01);
(Continued)

(58) Field of Classification Search
CPC ........ G01R 33/48; G16H 30/20; G16H 30/40; G06T 3/0012; G06T 3/0031;
(Continued)

(56) References Cited

U.S. PATENT DOCUMENTS

| 2010/0328311 A1* | 12/2010 | Lakshmanan | G06T 17/20 345/427 |
| 2021/0019939 A1* | 1/2021 | Hu | G06T 19/20 |

FOREIGN PATENT DOCUMENTS

| CN | 1781111 A | 5/2006 |
| CN | 108875813 A | 11/2018 |

(Continued)

OTHER PUBLICATIONS

International Search Report for PCT/CN2020/126487 dated Feb. 3, 2021.
(Continued)

*Primary Examiner* — Jacinta M Crawford
(74) *Attorney, Agent, or Firm* — The PL Law Group, PLLC

(57) ABSTRACT

A human face data processing method according to an embodiment of the present disclosure includes acquiring a picture of a human face by means of a scanning apparatus, obtaining point cloud information by means of a structured light stripe, and further obtaining a three-dimensional model of the human face, and mapping the three-dimensional model onto a circular plane in an area-preserving manner so as to form a two-dimensional human face image. Three-dimensional data is converted into two-dimensional data, thereby facilitating data storage. In addition, the three-dimensional data uses the area-preserving manner, such that the restoration quality is better when the two-dimensional data is restored to the three-dimension data, thereby facilitating the re-utilization of a three-dimensional image.

12 Claims, 7 Drawing Sheets

(51) Int. Cl.
*G06T 3/00* (2006.01)
*G06T 7/11* (2017.01)
*G06T 7/13* (2017.01)
*G06T 7/149* (2017.01)
*G06T 7/521* (2017.01)
*G06T 7/62* (2017.01)
*G06T 7/66* (2017.01)
*G06T 7/70* (2017.01)
*G06T 17/20* (2006.01)
*G06T 19/20* (2011.01)
*G16H 30/20* (2018.01)
*G16H 30/40* (2018.01)

(52) U.S. Cl.
CPC .......... *G06T 3/0031* (2013.01); *G06T 3/0037* (2013.01); *G06T 7/11* (2017.01); *G06T 7/13* (2017.01); *G06T 7/149* (2017.01); *G06T 7/521* (2017.01); *G06T 7/62* (2017.01); *G06T 7/66* (2017.01); *G06T 7/70* (2017.01); *G06T 17/20* (2013.01); *G06T 19/20* (2013.01); *G16H 30/20* (2018.01); *G16H 30/40* (2018.01); *G06T 2200/08* (2013.01); *G06T 2207/10024* (2013.01); *G06T 2207/10028* (2013.01); *G06T 2207/10081* (2013.01); *G06T 2207/10088* (2013.01); *G06T 2207/10108* (2013.01); *G06T 2207/20021* (2013.01); *G06T 2207/30016* (2013.01); *G06T 2207/30028* (2013.01); *G06T 2210/41* (2013.01); *G06T 2219/2008* (2013.01); *G06T 2219/2021* (2013.01)

(58) Field of Classification Search
CPC . G06T 3/0037; G06T 7/11; G06T 7/12; G06T 7/13; G06T 7/149; G06T 7/521; G06T 7/62; G06T 7/66; G06T 7/70; G06T 17/20; G06T 19/20; G06T 2200/08; G06T 2207/10024; G06T 2207/10028; G06T 2207/10081; G06T 2207/10088; G06T 2207/10108; G06T 2207/20021; G06T 2207/30016; G06T 2207/30028; G06T 2210/41; G06T 2219/2008; G06T 2219/2021

USPC ......................................................... 345/419
See application file for complete search history.

(56) References Cited

FOREIGN PATENT DOCUMENTS

| CN | 110046543 A | 7/2019 |
|---|---|---|
| CN | 110288642 A | 9/2019 |
| CN | 110473459 A | 11/2019 |
| CN | 110766808 A | 2/2020 |
| CN | 111127314 A | 5/2020 |
| JP | 2017-097439 A | 6/2017 |

OTHER PUBLICATIONS

Office action dated Feb. 19, 2020 from China Patent Office in a counterpart China Patent Application No. 201911361346.3 (all the cited references are listed in this IDS.) (English translation is also submitted herewith.).

Office action dated Jul. 17, 2023 from US Patent Office in a parent U.S. Appl. No. 17/773,932.

Havaei M, et al., "Within-brain classification for brain tumor segmentation", International journal of computer assisted radiology and surgery. May 2009;11 :777-88, 2016.

Wu Ming-Ni et al., "Brain tumor detection using color-based k-means clustering segmentation", In Third international conference on intelligent information hiding and multimedia signal processing, (IIH-MSP 2007), Nov. 26, 2007 (vol. 2, pp. 245-250).IEEE.

Shen Y et al., "Brain tumor segmentation on MRI with missing modalities", Information processing in Medical imaging: 26th International Conference, IPMI 2019, Hong Kong, China, Jun. 2-7, 2019, Proceedings 26 2019 (pp. 417-428).

Tu Z. et al.,, "Auto-context and its application to high-level vision tasks and 3D brain image segmentation", IEEE transactions on pattern analysis and machine intelligence. Dec. 1, 2009;32(10): 17 44-57.

* cited by examiner initializing the second weight of each harmonic mapping point, wherein at least three harmonic mapping points form one initial face — S4301 determining weighted dual points of each initial face, the weighted dual points having equal weighted distances to vertices of each initial face, wherein the weighted dual points are connected to form a dual face of the weighted dual points, and a plurality of dual faces determine a weighted Voronoi diagram — S4303 updating the second weight of each harmonic mapping point and readjusting the weighted Voronoi diagram according to the updated second weight — S4305

FIG. 7

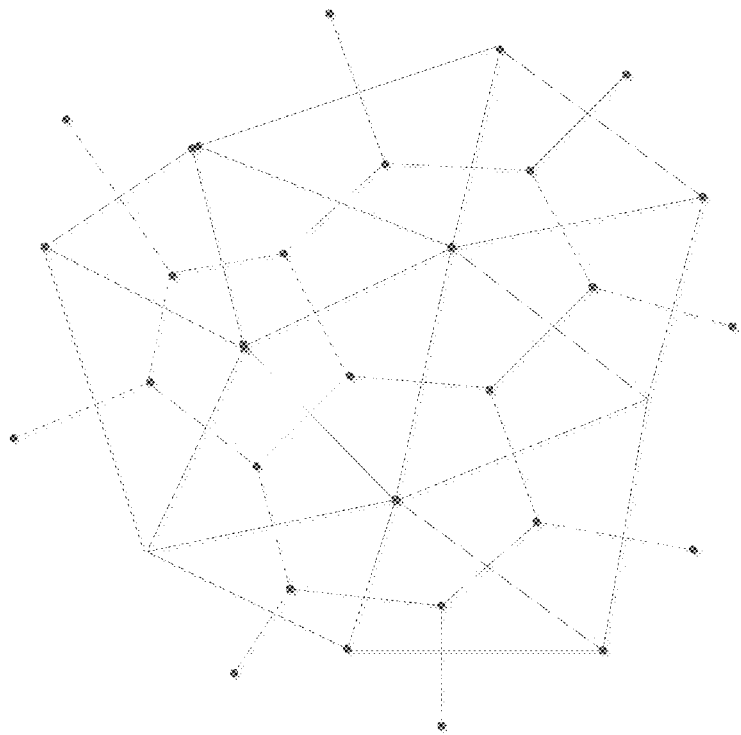

FIG. 8

HUMAN FACE DATA PROCESSING METHOD AND DEVICE, AND COMPUTER-READABLE STORAGE MEDIUM

CROSS-REFERENCE TO RELATED APPLICATIONS

This application claims benefit under 35 U.S.C. 119, 120, 121, or 365(c), and is a National Stage entry from International Application No. PCT/CN2020/126487, filed Nov. 4, 2020, which claims priority to the benefit of Chinese Patent Application Nos. 201911068702.2 filed on Nov. 5, 2019 and 201911361346.3 filed on Dec. 26, 2019 in the Chinese Intellectual Property Office, the entire contents of which are incorporated herein by reference.

BACKGROUND

1. Technical Field

The present invention relates generally to the field of iconology, and more particularly to the field of three-dimensional data.

2. Background Art

Generally, for a three-dimensional object, its corresponding three-dimensional data will typically include three-dimensional coordinates (X, Y, Z). In addition, color (RGB) and/or intensity information can also be included, and therefore, in order to store the three-dimensional data, a more complex storage format and larger storage space are generally required, so that it is inconvenient to store the data.

Furthermore, as compared with the three-dimensional data, analysis of two-dimensional data is relatively simple and less in computation, and therefore, if the three-dimensional data can be reduced to two-dimensional data, further study and analysis for the data are facilitated.

On the other hand, if the two-dimensional data is restored to the three-dimensional data, information of the original three-dimensional data needs to be kept as much as possible, and if too much information is lost in the process of dimensionality reduction, when restoring to the three-dimensional data from the two-dimensional data, problems such as distortion and the like will occur in the resulting three-dimensional image, which is not beneficial to further use of the three-dimensional image.

SUMMARY

It is an objective of the present disclosure to provide a method and device capable of optimizing the processing of human face data for the convenience of subsequent further use.

In the present invention, there is provided a human face data processing method, comprising: acquiring point cloud information of a human face scanned by a scanning apparatus, to obtain a three-dimensional model of the human face; and mapping the three-dimensional model onto a circular plane in an area-preserving manner, so as to form a two-dimensional human face image.

According to an embodiment of the present invention, the method further comprises: performing topology repair on the obtained three-dimensional model.

According to an embodiment of the present invention, wherein the performing topology repair on the obtained three-dimensional model comprises: determining positions of genera in the three-dimensional model; and eliminating the genera to reduce the number of the genera in the three-dimensional model.

According to an embodiment of the present invention, wherein the mapping the three-dimensional model onto a circular plane in an area-preserving manner comprises: determining a boundary of a two-dimensional plane; harmonically mapping the three-dimensional data to an interior of the boundary to form harmonic mapping points; calculating second weights of the harmonic mapping points, and further calculating a weighted Voronoi diagram of the harmonic mapping points; and mapping the three-dimensional model onto the two-dimensional plane in the area-preserving manner according to the weighted Voronoi diagram.

According to an embodiment of the present invention, wherein the determining a boundary of a two-dimensional plane comprises: determining a closed curve L in the three-dimensional model; storing points in the L into a linked list vlist, wherein vlist=$\{v_0, v_1, \ldots, v_{\{n-1\}}\}$, where $v_0$ and $v_n$ are one same point; calculating a length S of the L by:

$$s = \sum_{i=0}^{n-1} l_{v_i, v_{i+1}}$$

where $l_{v_i, v_{i+1}}$ is a length of an edge $[v_i, v_{i+1}]$; and
for each $v_i \in$ vlist, performing the following steps: calculating a length $s_i$ from the point $v_0$ to the point $v_i$, where $s_i = \sum_{j=1}^{i} l_{v_{j-1}, v_j}$; and according to an angle $\theta_i$ of the point $v_i$, where $$\theta_i = 2\pi \frac{s_i}{s},$$

determining a coordinate $\vec{f}(v_i) = (\cos\theta_i, \sin\theta_i)$ of each point.

According to an embodiment of the present invention, wherein the harmonically mapping the three-dimensional data onto an interior of the boundary to form harmonic mapping points comprises: initializing the three-dimensional data to form mapping points in the two-dimensional plane; calculating a harmonic energy between the mapping points in the two-dimensional plane; when the harmonic energy is greater than a preset energy gradient threshold, adjusting coordinates of the mapping points, and adjusting the harmonic energy according to the adjusted coordinates of the mapping points, and when the harmonic energy is less than the preset energy gradient threshold, stopping the adjustment; and taking, as the harmonic mapping points, coordinates of the mapping points when the adjustment is stopped.

According to an embodiment of the present invention, wherein the calculating a harmonic energy between the mapping points in the two-dimensional plane comprises: calculating a square value of differences between positions of adjacent mapping points; calculating a first product of the square value and a first weight of an edge formed by the adjacent mapping points; and calculating a sum of first products for all the mapping points.

According to an embodiment of the present invention, wherein the first weight of the edge formed by the adjacent mapping points is calculated by: determining an angle of a triangle that corresponds to the edge; if the edge is an edge common to two triangles, the first weight of the edge being equal to half of a sum of cotangent trigonometric functions of angles that are opposite to the edge in the two triangles; and if the edge is an edge on the boundary, the first weight of the edge being equal to half of a cotangent trigonometric function of an angle that is opposite to the edge in a triangle where the edge is located.

According to an embodiment of the present invention, wherein the calculating second weights of the harmonic mapping points, and further calculating a weighted Voronoi diagram of the harmonic mapping points comprises: initializing the second weight of each harmonic mapping point, w % herein at least three harmonic mapping points form one initial face; determining weighted dual points of each initial face, the weighted dual points having equal weighted distances to vertices of each initial face, wherein the weighted dual points are connected to form a dual face of the weighted dual points, and a plurality of dual faces determine a weighted Voronoi diagram; and updating the second weight of each harmonic mapping point, and readjusting the weighted Voronoi diagram according to the updated second weight.

According to an embodiment of the present invention, the updating the second weight of each harmonic mapping point comprises: determining an area $A_i$ of an initial face of each harmonic mapping point; determining an area $A_i'$ of a dual face of each harmonic mapping point; determining an area gradient $g_i=A_i-A_i'$ of each harmonic mapping point; determining a sum of squares of the area gradients of all the harmonic mapping points; and if the sum of squares is greater than a preset weight threshold, decreasing the second weight until the sum of squares is less than the weight threshold.

According to an embodiment of the present invention, the mapping the three-dimensional model onto the two-dimensional plane in the area-preserving manner according to the weighted Voronoi diagram comprises: determining a center of gravity of each dual face in the weighted Voronoi diagram; and mapping each of the harmonic mapping points to the center of gravity of each dual face, thereby mapping the three-dimensional model onto the two-dimensional plane in the area-preserving manner.

According to a second aspect of the present invention, there is provided a human face data processing device, comprising: a processor; and a memory connected with the processor, the memory having stored therein computer program code which, when executed, causes the processor to perform the method as described above.

According to a third aspect of the invention, there is provided a computer-readable storage medium having stored thereon computer-readable instructions which, when executed by one or more processors, implement the method as described above.

Advantageous effects of the technical solutions of the present invention include, but are not limited to, facilitating data storage when the three-dimensional data is converted into two-dimensional data. In addition, the three-dimensional data of the present invention uses the area-preserving manner such that the restoration quality is better when the two-dimensional data is restored to the three-dimension data, thereby facilitating the reutilization of the three-dimensional image.

BRIEF DESCRIPTION OF THE DRAWINGS

With reference to the accompanying drawings, the above features of the present invention can be better understood and its numerous objectives, features, and advantages are obvious to those skilled in the art, in which identical reference numerals refer to identical elements, and in which;

FIG. 7 illustrates a flow diagram of calculating second weights of the harmonic mapping points and further calculating a weighted Voronoi diagram of the harmonic mapping points according to an embodiment of the present invention:

FIG. 8 illustrates an example of a Voronoi diagram;

DETAILED DESCRIPTION

Technical solutions in embodiments of the present invention will be clearly and completely described below with reference to the drawings in the embodiments of the present invention. It is obvious that the embodiments described are only some of the embodiments of the present invention, not all of them. Based on the embodiments in the present invention, all other embodiments, which can be obtained by those skilled in the art without making any creative effort, fall within the protection scope of the present invention.

It should be understood that terms "first", "second", "third", and "fourth", etc. in the claims, description, and drawings of the present disclosure are used for distinguishing different objects, rather than describing a specific order. Terms "comprise" and "include" used in the description and claims of the present disclosure, indicate the presence of stated features, whole, steps, operations, elements, and/or components, but do not preclude the presence or addition of one or more other features, whole, steps, operations, elements, components, and/or combination thereof.

It should also be understood that terms used in the description of the present disclosure herein is for the purpose of describing specific embodiments only, but is not intended to limit the present disclosure. As used in the description and claims of this disclosure, "a", "an" and "the" in the singular form are intended to include the plural form, unless other circumstances are clearly indicated in the context. It should be further understood that a term "and/or" used in the description and claims of this disclosure refers to any and all possible combinations of one or more of associated listed items and comprises these combinations.

As used in the description and claims, a term "if" can be interpreted contextually as "when" or "once" or "in response to determining" or "in response to detecting". Similarly, a phrase "if determining" or "if detecting [a described condition or event]" can be interpreted contextually as meaning "once determining" or "in response to determining" or "once detecting [a described condition or event]" or "in response to detecting [a described condition or event]".

The specific embodiments of the present invention are described in detail below in conjunction with the accompanying drawings.

Figure 1:
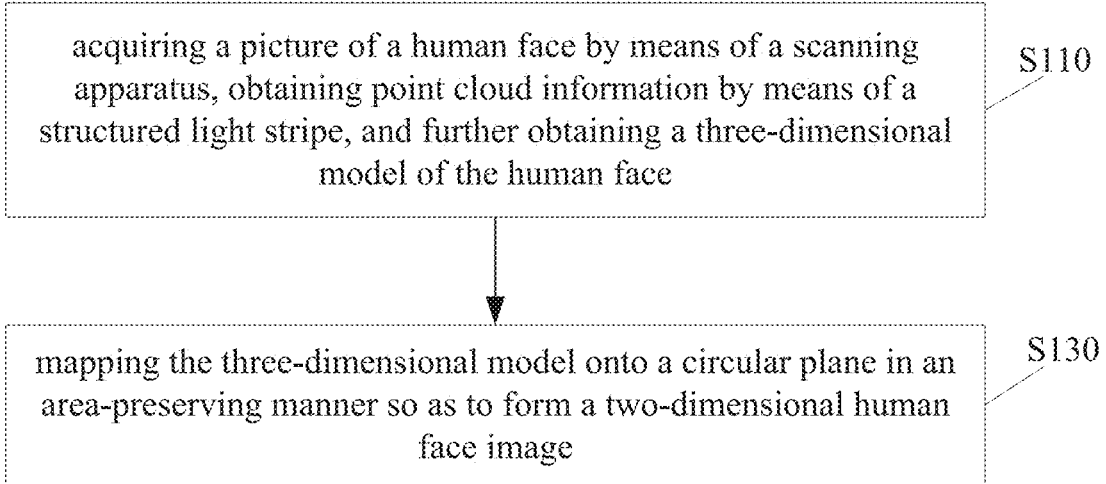
FIG. 1 illustrates a flow diagram of a human face data processing method according to an aspect of the present invention.

FIG. 1 illustrates a flow diagram of a human face data processing method according to an aspect of the present invention.

As shown in FIG. 1, the method of the present invention comprises: step S110, acquiring a picture of a human face by means of a scanning apparatus, obtaining point cloud information by means of a structured light stripe, and then obtaining a three-dimensional model of the human face; step S130, mapping the three-dimensional model onto a circular plane in an area-preserving manner, so as to form a two-dimensional human face image.

A point data set of an appearance surface of an object, which is obtained by a measuring instrument, is also called a point cloud, and generally, for a point cloud obtained by using a three-dimensional coordinate measuring machine and having less points between which there is a larger space, it is called a sparse point cloud; and for a point cloud obtained by using a three-dimensional laser scanner or a photographic scanner and having more and denser points, it is called a dense point cloud.

The point cloud can typically comprise three-dimensional coordinates (XYZ) and reflection intensity. In another embodiment, a point cloud obtained through a photogrammetry principle can comprise color information (RGB) in addition to the three-dimensional coordinates (XYZ). In another embodiment, a point cloud obtained by combining principles of laser measurement and photogrammetry can comprise the three-dimensional coordinates (XYZ), laser reflection intensity, and color information (RGB).

Due to the existence of the above information, the point cloud information can well represent more detailed human face information, and the denser the point cloud is, the more information it contains, and the higher its accuracy is when mapped.

The two-dimensional plane onto which the three-dimensional model of the human face is mapped can be in various shapes, but preferably, the two-dimensional plane can be a circle, because a shape of the human face is more similar to a circle, which is beneficial to reducing distortion in a mapping process and shortening a convergence time of an algorithm.

In addition, the mapping in the present invention is performed in the area-preserving manner, thereby effectively preserving area information in the human face, so that information loss can be reduced when the three-dimensional human face data is restored to, and the availability of the three-dimensional human face image is better.

Figure 2:
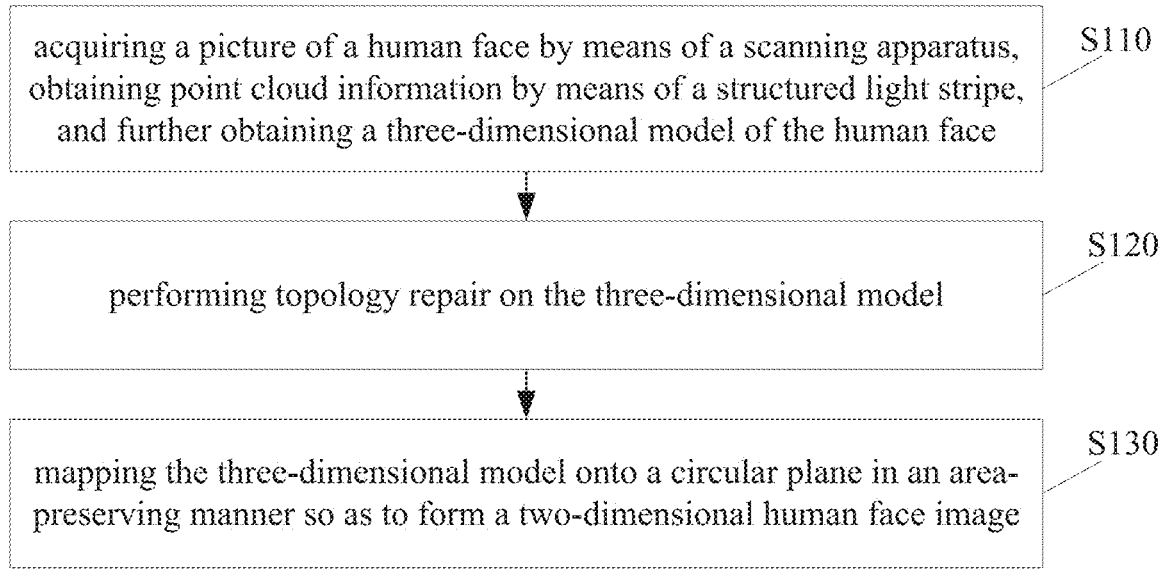
FIG. 2 illustrates a flow diagram of a human face data processing method according to another aspect of the present invention.

According to an embodiment of the present invention, as shown in FIG. 2, the present invention can further comprise, step S120, performing topology repair on the three-dimensional model. The topology repair is geometric shape repair, to repair the imported model into a curved surface with a closed shape, so that the model becomes a whole. Geometry without the topology repair may have face or line missing, or face connection errors.

It can be appreciated that there are typically many false genera (handles and tunnels) in the three-dimensional model due to image segmentation errors. These false genera need to be detected and eliminated.

These handles are too tiny to be detected directly by naked eyes. A practical method is to obtain them by methods of calculating topology that usually depend on algorithms of handle loops and tunnel loops of the curved surface. After these false handles are obtained, they are cut along the handle loops, and then gaps are filled to remove topological noise.

Figure 3:
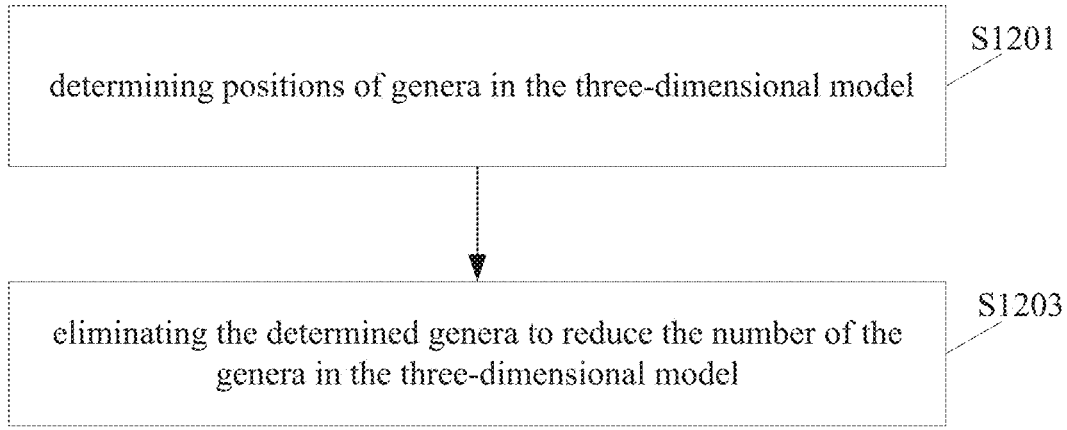
FIG. 3 illustrates a flow diagram of a method of performing topology repair on a formed three-dimensional model according to an aspect of the present invention.

Therefore, according to an embodiment of the present invention, as shown in FIG. 3, the performing topology repair on the obtained three-dimensional model comprises: step S1201, determining positions of genera in the three-dimensional model; and step S1203, eliminating the determined genera to reduce the number of the genera in the three-dimensional model.

Reducing the number of the genera in the three-dimensional model as described above, preferably, is to reduce the number of the genera to zero, i.e., to achieve a zero-genus three-dimensional model, which will help to improve the accuracy of mapping the three-dimensional model onto the two-dimensional plane.

A method of mapping the three-dimensional model onto the two-dimensional plane in the area-preserving manner is described in detail below.

It should be appreciated that there are variety manners of mapping the three-dimensional model onto the two-dimensional plane. For example, a three-dimensional model can be mapped onto a two-dimensional plane in a conformal manner, but this manner has a certain drawback because the conformal manner will cause area information of a three-dimensional object to be lost, so that information is lost when the two-dimensional image is restored to the three-dimensional image again.

In the present invention, however, it is in the area-preserving mapping manner that the three-dimensional object is mapped into the two-dimensional plane, so that areas of all parts in the three-dimensional object are still kept unchanged in the two-dimensional plane, to facilitate subsequent further processing.

Figure 4:
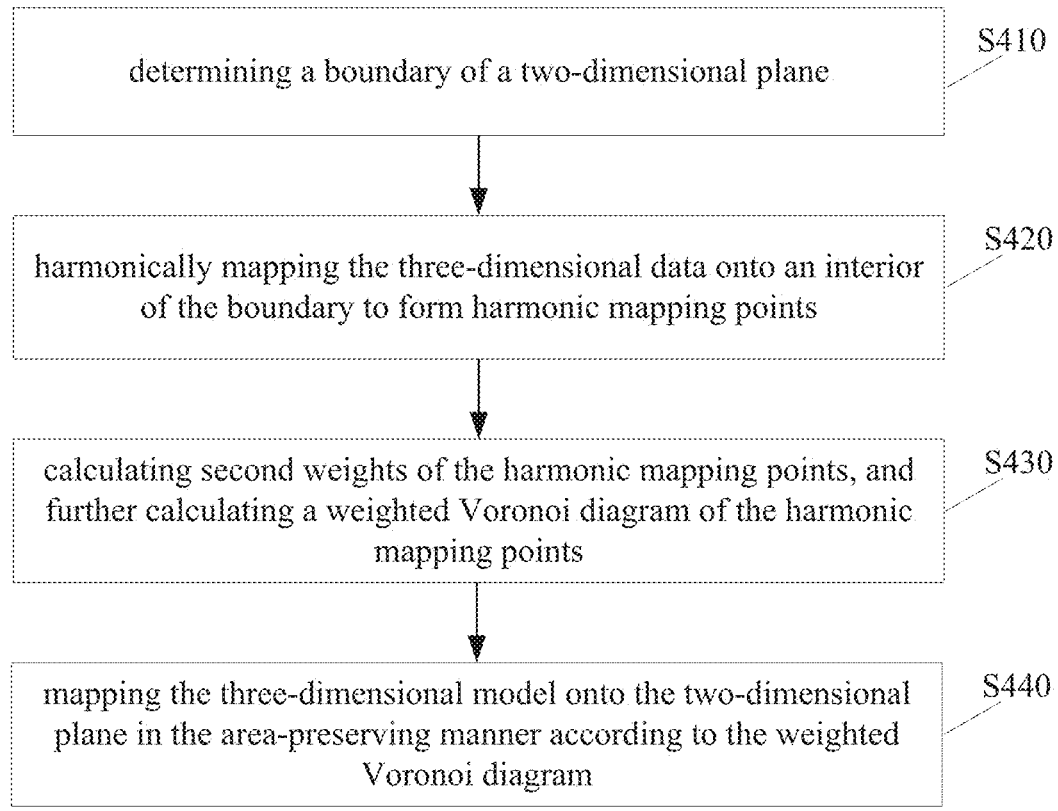
FIG. 4 illustrates a flow diagram of a method of mapping the three-dimensional model onto a circular plane in an area-preserving manner according to an embodiment of the present disclosure.

FIG. 4 illustrates a flow diagram of a method of mapping the three-dimensional model onto a circular plane in an area-preserving manner according to an embodiment of the present disclosure, comprising: step S410, determining a boundary of the two-dimensional plane; step S420, harmonically mapping the three-dimensional data to an interior of the boundary to form harmonic mapping points; step S430, calculating second weights of the harmonic mapping points, and further calculating a weighted Voronoi diagram of the harmonic mapping points; and step S440, mapping the three-dimensional model onto the two-dimensional plane in the area-preserving manner according to the weighted Voronoi diagram.

It can be learn from the above that, in the present invention, the three-dimensional human face is mapped onto the two-dimensional plane that is circular, so that the two-dimensional boundary is a circle.

According to an embodiment of the present invention, the determining a boundary of the two-dimensional plane can comprise: determining a closed curve L in the three-dimensional model; storing points in the L into a linked list vlist, where vlist=$\{v_0, v_1, \ldots, v_{\{n-1\}}\}$, where $v_0$ and $v_n$ are one same point; and calculating a length S of the L by:

$$s = \sum_{i=0}^{n-1} l_{v_i, v_{i+1}}$$

where $l_{v_i, v_{i+1}}$ is a length of an edge $[v_i, v_{i+1}]$; and for each $v_i \in \text{vlist}$, performing the following steps: calculating a length $s_i$ from the point $v_0$ to the point $v_i$, where $s_i = \sum_{j=1}^{i} l_{v_{j-1}, v_j}$; according to an angle $\theta_i$ of the point $v_i$, where $$\theta_i = 2\pi \frac{s_i}{s};$$

and determining a coordinate $\vec{f}(v_i) = (\cos\theta_i, \sin\theta_i)$ of each point.

It can be seen from the above that the determined boundary of the circle is actually a boundary of a polygon, and the more sampling points are taken, the closer the polygon is to the circle.

It can also be seen from the above that the above coordinate of the point is actually a polar coordinate. It should be understood that the polar coordinate is merely one manner, and any other type of coordinate system can also be adopted.

After the boundary is determined, points in the three-dimensional data that are non-boundary can be mapped to the interior of the two-dimensional plane defined by the boundary. The three-dimensional data can be mapped onto the two-dimensional plane by means of the harmonic mapping.

Expressed in a popular way, when the three-dimensional model is mapped onto the two-dimensional plane, interior parts of the model can also, in themselves, receive certain tensile force due to deformation of the boundary and then spread towards the boundary, and a spreading direction of each point is a result of a resultant force of all points around the point. Until each part no longer changes, it amounts to reaching a "harmonic" state.

Figure 5:
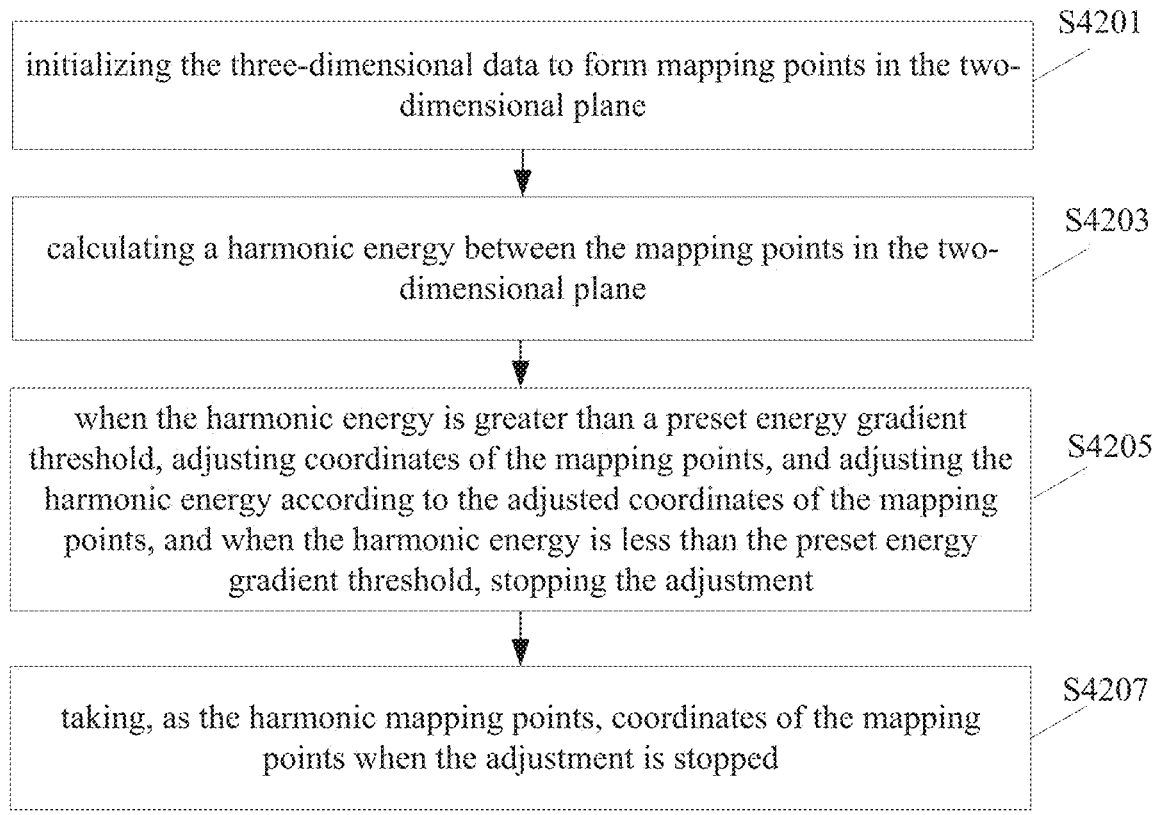
FIG. 5 illustrates a flow diagram of harmonically mapping three-dimensional data to an interior of a boundary to form harmonic mapping points.

FIG. 5 illustrates a flow diagram of harmonically mapping three-dimensional data to an interior of a boundary to form harmonic mapping points.

As shown in FIG. 5, the harmonically mapping the three-dimensional data to an interior of the boundary to form harmonic mapping points S420 comprises: step S4201, initializing the three-dimensional data to form mapping points in the two-dimensional plane; step S4203, calculating a harmonic energy between the mapping points in the two-dimensional plane; step S4205, when the harmonic energy is greater than a preset energy gradient threshold, adjusting coordinates of the mapping points, and adjusting the harmonic energy according to the adjusted coordinates of the mapping points, and when the harmonic energy is less than the preset energy gradient threshold, stopping the adjustment; and, step S4207, taking, as the harmonic mapping points, coordinates of the mapping points when the adjustment is stopped.

The above steps are specifically described below.

For a mesh M, an energy gradient threshold $\delta E$ is preset.

For a non-boundary point, it is initialized to $\vec{f} = (0,0)$, where $\vec{f}$ represents a position of the point in the two-dimensional image. According to an embodiment of the present invention, all the three-dimensional data points can be mapped into the two-dimensional plane described above, and initially, all the three-dimensional points can be mapped to a position (0, 0), which is, of course, only one example, and initially, all the three-dimensional points can also be mapped into the two-dimensional plane evenly. i.e. all the points are equidistant in the two-dimensional plane.

Next, an initial harmonic energy is calculated, that is, the harmonic energy between the above mapping points in the two-dimensional plane is calculated. A harmonic energy calculation equation is as follow:

$$E(f) = \Sigma_{[v_i, v_j] \in M} k_{ij} (f(v_j) - f(v_i))^2 \quad \text{Equation 1}$$

In the above equation, E(f) represents the harmonic energy of all the mapping points; it can be understood that the initial harmonic energy may be maximum, and thereafter the position of each mapping point will be gradually adjusted so that the harmonic energy gradually decreases and finally falls below the preset energy gradient threshold. At this time, the harmonic state can be reached.

In the above equation, the energy between all the points belonging to the two-dimensional plane (excluding the boundary points) and their adjacent points is calculated, and according to an embodiment of the present invention, a square value of differences between positions of adjacent mapping points is first calculated; a first product of the square value and a first weight of an edge formed by the adjacent mapping points is calculated; and a sum of first products for all the mapping points is calculated to obtain the initial harmonic energy.

If the initial harmonic energy is greater than the energy gradient threshold $\delta E$, positions of corresponding points are adjusted and a new harmonic energy E is recalculated, and the harmonic energy calculated in the previous round is set as $E_0$.

Next, a difference between the new harmonic energy E and the harmonic energy $E_0$ calculated in the previous round is calculated, i.e., whether $|E - E_0|$ is greater than the preset harmonic energy gradient $\delta E$. This cycle is continued until the difference between the new harmonic energy E and the harmonic energy $E_0$ calculated in the previous round is not greater than the preset harmonic energy gradient threshold $\delta E$. At this time, the energy gradient between all the points is minimum, so that the harmonic state is reached.

The coordinate of each mapping point is calculated by:

$$\vec{f}(v_i) = \sum_{[v_i, v_j] \in M} \frac{k_{ij} \vec{f}(v_j)}{\sum_j k_{ij}} \quad \text{equation 2}$$

where $v_i$ is a representation of the i-th point, $v_j$ is a representation of the j-th point adjacent to i, $f(v_i)$ represents a position of the point $v_i$, and M represents a triangular mesh curved surface, $k_{ij}$ is a weight of an edge $[v_i, v_j]$.

According to an embodiment of the present disclosure, the first weight of the edge formed by the adjacent mapping points is calculated by: determining an angle of a triangle that corresponds to the edge; if the edge is an edge common to two triangles, the first weight of the edge being equal to half of a sum of cotangent trigonometric functions of angles that are opposite to the edge in the two triangles; and if the edge is an edge on the boundary, the first weight of the edge being equal to half of a cotangent trigonometric function of an angle that is opposite to the edge in a triangle where the edge is located.

Figure 6:
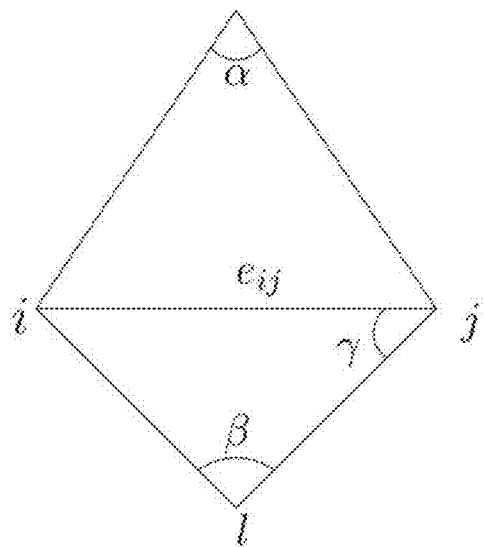
FIG. 6 illustrates a schematic diagram of calculating a weight of each edge.

For the triangular mesh, there are generally two cases for triangle's edges, where one is an edge common to two triangles and the other is an edge of the boundary, as shown in FIG. 6.

In FIG. 6, an edge determined by points i and j is an edge common to two triangles, and an edge determined by points i and l is an edge of the boundary, angles of the two triangles that correspond to the edge $e_{ij}$ are α and β, respectively, and an angle of a triangle that corresponds to the edge $e_{il}$ is γ, and therefore, weights of the two edges are respectively calculated by:

$$k_{if} = \omega(e_{ij}) = \frac{1}{2}(\cot\alpha + \cot\beta)$$

edge of the interior (having two adjacent faces)

$$k_{il} = \omega(e_{il}) = \frac{1}{2}\cot\gamma$$

edge of the boundary (having only one face)

It can be seen that as the positions of the points are continuously adjusted, the angle of each triangle continuously changes, and therefore the weight of the edge continuously changes. But due to the convergence of this adjustment, the weight of the edge will gradually remain constant, so that the mapping of the image reaches the harmonic state.

In other words, it can be seen from the above description that, with the adjustment of each mapping point, the harmonic energy gradually decreases, and eventually reaches less than the specific harmonic energy gradient threshold, thereby implementing the harmonic mapping.

FIG. 7 illustrates a flow diagram of calculating second weights of harmonic mapping points and further calculating a weighted Voronoi diagram of the harmonic mapping points according to an embodiment of the present invention.

As shown in FIG. 7, in the present invention, the calculating second weights of the harmonic mapping points and further calculating a weighted Voronoi diagram of the harmonic mapping points comprises:

step S4301, initializing the second weight of each harmonic mapping point, wherein at least three harmonic mapping points form one initial face; step S4303, determining weighted dual points of each initial face, the weighted dual points having equal weighted distances to vertices of each initial face, wherein the weighted dual points are connected to form a dual face of the weighted dual points, and a plurality of dual faces determine a weighted Voronoi diagram; and, step S4305, updating the second weight of each harmonic mapping point and readjusting the weighted Voronoi diagram according to the updated second weight.

First, according to an embodiment of the present invention, the weighted Voronoi diagram is determined on the basis of the formed harmonic mapping points. FIG. 8 illustrates an example of a Voronoi diagram.

As shown in FIG. 8, the Voronoi diagram is a dual form of a mesh (not limited to a triangular mesh), and taking the triangular mesh as an example, for each face in the mesh, it corresponds to one dual point (vertex of a dotted line) in the Voronoi diagram, the dual point has equal distances to three vertices (i.e., the harmonic mapping points in the above, vertices of solid lines in FIG. 8), and each point (harmonic mapping point in the present invention) in the original mesh also corresponds to one dual face in the Voronoi diagram, as shown in FIG. 8. However, the weighted Voronoi diagram is different from an ordinary Voronoi diagram in that each point in the original mesh has a weight, and the distance is calculated originally by $d=\|v-q\|^2$, and after the weighting, by $d=\|v-q\|^2+\omega$, so that the adding of the weight ω will make a size of a Voronoi cell change with the weight. The greater weight a vertex of a certain face has, the farther Euclidean distance a circumcenter of the face has to the vertex, so that an area of a dual face corresponding to the vertex will become larger.

The method of FIG. 7 is specifically explained below.

First, a weight of each point is initialized to $\omega_i=0$, and a weight threshold ε is given, for example, $\varepsilon=10^{-3}$.

For each face $f_i=[v_a,v_b,v_c]$ in the M, its weighted dual point $q_i$ is calculated using the following system of equations, where $v_a$, $v_b$, $v_c$ represent three vertices of each solid-line triangle:

$$\begin{cases} 2(v_a - v_b)^T q_i = \|v_a\|^2 - \|v_b\|^2 + \omega_a - \omega_b \\ 2(v_b - v_c)^T q_i = \|v_b\|^2 - \|v_c\|^2 + \omega_b - \omega_c \end{cases} \quad \text{equation 3}$$

i.e., $q_i$ has equal weighted distances d to these three points, and $d(q,v)=|v-q|^2+\omega_v$.

d(q, v) is a weighted distance of q and v, and $\omega_v$ is a weight of a point v.

For each solid-line edge in the M, weighted dual points q on both sides of the solid-line edge are connected to form a new dotted-line edge as a dual edge of the solid-line edge.

A new diagram formed by these dual edges is the weighted Voronoi diagram Ω. Each harmonic mapping point, in the weighted Voronoi diagram Ω, corresponds to one dual face, which is one cell $Cell_i$, then a current area of each point is $A'_i=\text{area}(Cell_i)$.

A gradient $g_i=A_i-A'_i$ of each point is calculated, and let $G=\{g_0, g_1, \ldots, g_n\}$, if $\|G\|^2<\varepsilon$, iterative updating is stopped, otherwise, let $\omega_i=\omega_i-\lambda g_i$, where λ is a step of the gradient descent, needs self-adjustment, and is generally set to be a value less than 1, and a new weight can also be iteratively calculated using a Newton method and the like. $A_i$ is a target area of each harmonic mapping point, i.e., an area in the three-dimensional object that the harmonic mapping point corresponds to.

Figure 9:
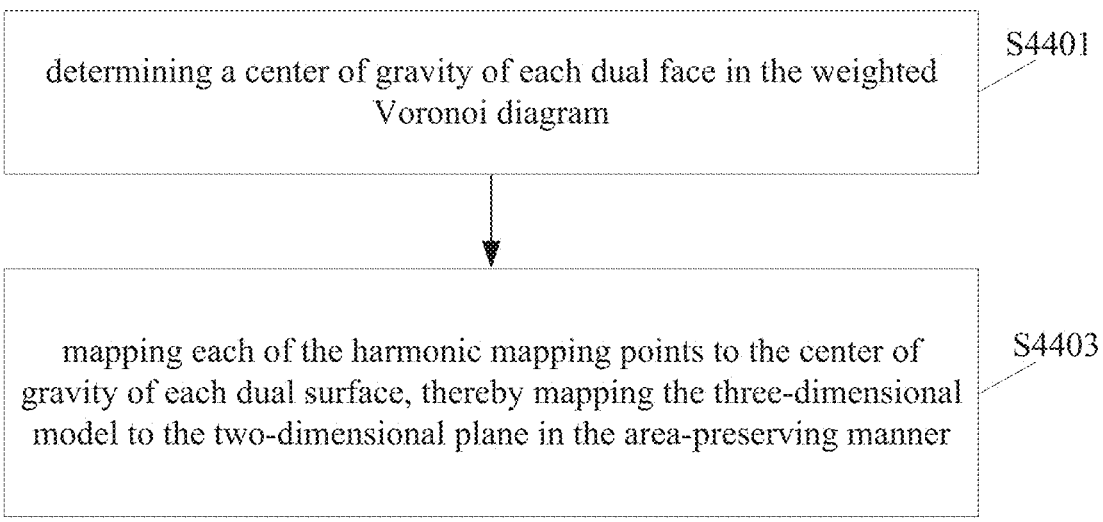
FIG. 9 illustrates a flow diagram of mapping the three-dimensional model onto a two-dimensional plane in an area-preserving manner according to an embodiment of the present invention.

FIG. 9 illustrates a flow diagram of mapping the three-dimensional model onto a two-dimensional plane in an area-preserving manner according to an embodiment of the present invention.

As shown in FIG. 9, the mapping the three-dimensional model onto the two-dimensional plane in the area-preserving manner according to the weighted Voronoi diagram comprises: step S4401, determining a center of gravity of each dual face in the weighted Voronoi diagram; step S4403, mapping each of the harmonic mapping points to the center of gravity of each dual surface, thereby mapping the three-dimensional model to the two-dimensional plane in the area-preserving manner.

Therefore, the three-dimensional data of the human face can be mapped into the two-dimensional plane in the area-preserving manner by means of the above method.

Figure 10A:
FIGS. 10A, 10B, and 10C illustrate an original of a three-dimensional image, a two-dimensional image after harmonic mapping, and a two-dimensional image after area-preserving mapping, respectively.
Figure 10B:
Figure 10C:

FIGS. 10A, 10B, and 10C illustrate an original of a three-dimensional image, a two-dimensional image after harmonic mapping, and a two-dimensional image after area-preserving mapping, respectively.

As shown in FIG. 10A, it is an image of an ordinary human face, from which three-dimensional information of the human face can be extracted and a three-dimensional model is constructed.

As shown in FIG. 10B, it is a two-dimensional image formed after the human face of FIG. 10A has been subjected to the harmonic mapping. In the two-dimensional image, the angle is preserved, but an area of each part is not the same as that of the three-dimensional image.

In FIG. 10C is a two-dimensional image formed after the two-dimensional image of FIG. 10B has been subjected to further area-preserving mapping. In the two-dimensional image, points in FIG. 10B have been subjected to further stretching and adjustment. It should be appreciated that, in the image of FIG. 10C, part of angle information is preserved, and part of area and shape information is also preserved.

According to the present invention, the storage of the three-dimensional data is facilitated, and according to the present invention, the area and shape information of the image can be preserved, thereby facilitating not losing the area and shape information when the two-dimensional image is restored to the three-dimensional image.

The foregoing can be better understood in light of the following articles:

A1. A human face data processing method, comprising: acquiring point cloud information of a human face by means of a scanning apparatus to obtain a three-dimensional model of the human face; and mapping the three-dimensional model onto a circular plane in an area-preserving manner so as to form a two-dimensional human face image.

A2. The method of A1, further comprising: performing topology repair on the formed three-dimensional model.

A3. The method of A1 or A2, wherein the performing topology repair on the formed three-dimensional model comprises: determining positions of genera in the three-dimensional model; and eliminating the genera to reduce the number of the genera in the three-dimensional model.

A4. The method of any of A1 to A3, wherein the mapping the three-dimensional model onto a circular plane in an area-preserving manner comprises: determining a boundary of a two-dimensional plane; harmonically mapping the three-dimensional data to an interior of the boundary to form harmonic mapping points; calculating second weights of the harmonic mapping points, and further calculating a weighted Voronoi diagram of the harmonic mapping points; and mapping the three-dimensional model onto the two-dimensional plane in the area-preserving manner according to the weighted Voronoi diagram.

A5. The method of any of A1 to A4, wherein the determining a boundary of a two-dimensional plane comprises: determining a closed curve L in the three-dimensional model; storing points in the L into a linked list vlist, wherein vlist={$v_0, v_1, \ldots, v_{(n-1)}$}, $v_0$ and $v_n$ are one same point; calculating a length S of the L by:

$$s = \sum_{i=0}^{n-1} l_{v_i, v_{i+1}}$$

where $l_{v_i, v_{i+1}}$ is a length of an edge $[v_i, v_{i+1}]$; and
for each $v_i \in$ vlist, performing the following steps: calculating a length $s_i$ from the point $v_0$ to the point $v_i$, where $s_i = \sum_{j=1}^{i} l_{v_{j-1}, v_j}$; according to an angle $\theta_i$ of the point $v_i$, where $$\theta_i = 2\pi \frac{s_i}{s},$$

determining a coordinate $\vec{f}(v_i) = (\cos\theta_i, \sin\theta_i)$ of each point.

A6. The method of any of A1 to A5, wherein the harmonically mapping the three-dimensional data to an interior of the boundary to form harmonic mapping points comprises: initializing the three-dimensional data to form mapping points in the two-dimensional plane; calculating a harmonic energy between the mapping points in the two-dimensional plane; when the harmonic energy is greater than a preset energy gradient threshold, adjusting coordinates of the mapping points, and adjusting the harmonic energy according to the adjusted coordinates of the mapping points, and when the harmonic energy is less than the preset energy gradient threshold, stopping the adjustment; and taking, as the harmonic mapping points, coordinates of the mapping points when the adjustment is stopped.

A7. The method of any of A1 to A6, wherein the calculating a harmonic energy between the mapping points in the two-dimensional plane comprises: calculating a square value of differences between positions of adjacent mapping points; calculating a first product of the square value and a first weight of an edge formed by the adjacent mapping points; and calculating a sum of the first products for all the mapping points.

A8. The method of any of A1 to A7, wherein the first weight of the edge formed by the adjacent mapping points is calculated by: determining an angle of a triangle that corresponds to the edge; if the edge is an edge common to two triangles, the first weight of the edge being equal to half of a sum of cotangent trigonometric functions of angles that are opposite to the edge in the two triangles; and if the edge is an edge on the boundary, the first weight of the edge being equal to half of a cotangent trigonometric function of an angle that is opposite to the edge in a triangle where the edge is located.

A9. The method of any of A1 to A8, wherein the calculating second weights of the harmonic mapping points and further calculating a weighted Voronoi diagram of the harmonic mapping points comprises: initializing the second weight of each harmony mapping point, wherein at least three harmony mapping points form one initial face; determining weighted dual points of each initial face, the weighted dual points having equal weighted distances to vertices of each initial face, wherein the weighted dual points are connected to form a dual face of the weighted dual points, and a plurality of dual faces determine a weighted Voronoi diagram; and updating the second weight of each harmony mapping point, and readjusting the weighted Voronoi diagram according to the updated second weight.

A10. The method of any of A1 to A9, wherein the updating the second weight of each harmonic mapping point comprises: determining an area $A_i$ of an initial face of each harmonic mapping point; determining an area $A_i'$ of a dual face of each harmonic mapping point; determining an area gradient $g_i = A_i - A_i'$ of each harmonic mapping point; determining a sum of squares of the area gradients of all the harmonic mapping points; and if the sum of squares is greater than a preset weight threshold, decreasing the second weight until the sum of squares is less than the weight threshold.

A11. The method of any of A1 to A10, wherein the mapping the three-dimensional model onto the two-dimensional plane in the area-preserving manner according to the weighted Voronoi diagram comprises: determining a center of gravity of each dual face in the weighted Voronoi diagram; and mapping each of the harmonic mapping points to the center of gravity of each dual face, thereby mapping the three-dimensional model onto the two-dimensional plane in the area-preserving manner.

A12. A human face data processing device, comprising: a processor; and a memory connected with the processor, the memory having stored therein computer program code which, when executed, causes the processor to perform the method of any of A1 to A11.

A13. A computer-readable storage medium having stored thereon computer-readable instructions which, when executed by one or more processors, implement the method of any of A1 to A11.

Exemplary Device

It can be appreciated by those skilled in the art that, various aspects of the present invention can be implemented as a system, method or program product. Accordingly, the various aspects of the present invention can be specifically implemented in the following form: an entire hardware embodiment, an entire software embodiment (comprising firmware, microcode, etc.), or an embodiment combining hardware and software aspects, which can be collectively called a "circuit", "module", or "system" herein.

In some possible embodiments, a device for testing an application according to an embodiment of the present invention can comprise at least one processing unit, and at least one storage unit. The storage unit has stored therein program code which, when executed by the processing unit, causes the processing unit to perform the steps in the method of testing the application according to various exemplary embodiments of the present invention as described in the above "exemplary method" section of this specification.

Exemplary Program Product

In some possible embodiments, the various aspects of the present invention can also be implemented in a form of a program product comprising program code which, when the program product is run on the device, causes the device to perform the steps in the method of testing the application according to various exemplary embodiments of the present invention as described in the above "exemplary method" section of this specification.

The program product can employ any combination of one or more readable media. The readable medium can be a readable signal medium or a readable storage medium. The readable storage medium can be, for example, but is not limited to, an electronic, magnetic, optical, electromagnetic, infrared, or semiconductor system, apparatus, or device, or any combination of the above. More specific examples (a non-exhaustive list) of the readable storage medium comprise: an electrical connection having one or more wires, a portable diskette, a hard disk, a random access memory (RAM), a read-only memory (ROM), an erasable programmable read-only memory (EPROM or flash memory), an optical fiber, a portable compact disc read-only memory (CD-ROM), an optical storage device, a magnetic storage device, or any suitable combination of the above.

The readable signal medium can comprise a data signal propagated in baseband or as part of a carrier wave, in which readable program code is carried. Such a propagated data signal can take a variety of forms, comprising, but not limited to, an electro-magnetic signal, an optical signal, or any suitable combination of the above. The readable signal medium can also be any readable medium other than the readable storage medium, wherein the readable medium can send, propagate, or transmit a program for use by or in conjunction with an instruction execution system, apparatus, or device.

Program code contained on the readable medium can be transmitted using any appropriate medium, comprising but not limited to wireless, wired, optical cable, RF, etc., or any suitable combination of the above.

Program code for performing operations of the present invention can be written in any combination of one or more programming languages, wherein the programming language comprises an object-oriented programming language such as Java, C++ or the like and also comprises a conventional procedural programming language such as the "C" programming language or a similar programming language. The program code can be executed entirely on a user computing device, partly on the user computing device and partly on a remote computing device, or entirely on the remote computing device or a server. In the case where the remote computing device is involved, the remote computing device can be connected to the user computing device through any kind of network, comprising a local area network (LAN) or a wide area network (WAN), or can be connected to an external computing device (e.g., through the Internet using an internet service provider).

It should be noted that although several units or sub-units of the device are mentioned in the above detailed description, such a division is merely illustrative and not mandatory. In fact, features and functions of two or more units described above can be embodied in one unit according to the embodiments of the present invention. Conversely, features and functions of one unit described above can be further divided and embodied in a plurality of units.

Furthermore, while operations of the methods of the present invention are depicted in the drawings in a specific order, this does not require or imply that these operations must be performed in this specific order, or that all of the illustrated operations must be performed, to achieve desirable results. Additionally or alternatively, certain steps can be omitted, multiple steps can be combined into one step for execution, and/or one step can be broken down into multiple steps for execution.

While the spirit and principles of the present invention have been described with reference to several specific embodiments, it should be understood that the present invention is not limited to the disclosed embodiments, and the division of various aspects does not mean that the features in these aspects cannot be combined to benefit, but is only for the convenience of expression. The present invention is intended to cover various modifications and equivalent arrangements included within the spirit and scope of the attached claims.

What is claimed is:

1. A human face data processing method, comprising:
acquiring a picture of a human face by means of a scanning apparatus, obtaining point cloud information by means of a structured light stripe, and further obtaining a three-dimensional model of the human face; and
mapping the three-dimensional model onto a circular plane in an area-preserving manner so as to form a two-dimensional human face image,
wherein the mapping of the three-dimensional model comprises:
determining a boundary of a two-dimensional plane;
harmonically mapping the three-dimensional data to an interior of the boundary to form harmonic mapping points;
calculating second weights of the harmonic mapping points, and further calculating a weighted Voronoi diagram of the harmonic mapping points; and
mapping the three-dimensional model onto the two-dimensional plane in the area-preserving manner according to the weighted Voronoi diagram.

2. The method of claim 1, further comprising: performing topology repair on the obtained three-dimensional model.

3. The method of claim 2, wherein the performing topology repair on the obtained three-dimensional model comprises:
    determining positions of genera in the three-dimensional model; and
    eliminating the genera to reduce the number of the genera in the three-dimensional model.

4. The method of claim 1, wherein the determining a boundary of a two-dimensional plane comprises:
    determining a closed curve L in the three-dimensional model;
    storing points in the L into a linked list vlist, where vlist=$\{v_0, v_1, \ldots, v_{\{n-1\}}\}$, $v_0$ and $v_n$ are one same point;
    calculating a length S of the L by:

$$s = \sum_{i=0}^{n-1} l_{v_i, v_{i+1}}$$

where $l_{v_i, v_{i+1}}$ is a length of an edge $[v_i, v_{i+1}]$; and
    for each $v_i \in$ vlist, performing the following steps:
    calculating a length $s_i$ from the point $v_0$ to the point $v_i$, where $s_i = \sum_{j=1}^{i} l_{v_{j-1}, v_j}$;
    according to an angle $\theta_i$ of the point $v_i$, where $$\theta_i = 2\pi \frac{s_i}{s};$$

determining a coordinate $\vec{f}(v_i) = (\cos\theta_i, \sin\theta_i)$ of each point.

5. The method of claim 1, wherein the harmonically mapping the three-dimensional data to an interior of the boundary to form harmonic mapping points comprises:
    initializing the three-dimensional data to form mapping points in the two-dimensional plane;
    calculating a harmonic energy between the mapping points in the two-dimensional plane;
    when the harmonic energy is greater than a preset energy gradient threshold, adjusting coordinates of the mapping points, and adjusting the harmonic energy according to the adjusted coordinates of the mapping points, and when the harmonic energy is less than the preset energy gradient threshold, stopping the adjustment; and
    taking, as the harmonic mapping points, coordinates of the mapping points when the adjustment is stopped.

6. The method of claim 5, wherein the calculating a harmonic energy between the mapping points in the two-dimensional plane comprises:
    calculating a square value of differences between positions of adjacent mapping points;
    calculating a first product of the square value and a first weight of an edge formed by the adjacent mapping points; and
    calculating a sum of the first products for all the mapping points.

7. The method of claim 6, wherein the first weight of the edge formed by the adjacent mapping points is calculated by:
    determining an angle of a triangle that corresponds to the edge;
    if the edge is an edge common to two triangles, the first weight of the edge being equal to half of a sum of cotangent trigonometric functions of angles that are opposite to the edge in the two triangles; and
    if the edge is an edge on the boundary, the first weight of the edge being equal to half of a cotangent trigonometric function of an angle that is opposite to the edge in a triangle where the edge is located.

8. The method of claim 1, wherein the calculating second weights of the harmonic mapping points and further calculating a weighted Voronoi diagram of the harmonic mapping points comprises:
    initializing the second weight of each harmony mapping point, wherein at least three harmony mapping points form one initial face;
    determining weighted dual points of each initial face, the weighted dual points having equal weighted distances to vertices of each initial face, wherein the weighted dual points are connected to form a dual face of the weighted dual points, and a plurality of dual faces determine a weighted Voronoi diagram; and
    updating the second weight of each harmony mapping point, and readjusting the weighted Voronoi diagram according to the updated second weight.

9. The method of claim 8, wherein the updating the second weight of each harmonic mapping point comprises:
    determining an area $A_i$ of an initial face of each harmonic mapping point;
    determining an area $A_i'$ of a dual face of each harmonic mapping point;
    determining an area gradient $g_i = A_i - A_i'$ of each harmonic mapping point;
    determining a sum of squares of the area gradients of all the harmonic mapping points; and
    if the sum of squares is greater than a preset weight threshold, decreasing the second weight until the sum of squares is less than the weight threshold.

10. The method of claim 1, wherein the mapping the three-dimensional model onto the two-dimensional plane in the area-preserving manner according to the weighted Voronoi diagram comprises:
    determining a center of gravity of each dual face in the weighted Voronoi diagram; and
    mapping each of the harmonic mapping points to the center of gravity of each dual face, thereby mapping the three-dimensional model onto the two-dimensional plane in the area-preserving manner.

11. A human face data processing device, comprising:
    a processor; and
    a memory connected with the processor, the memory having stored therein computer program code which, when executed, causes the processor to perform a human face data processing method, the human face data processing method comprising:
    acquiring a picture of a human face by means of a scanning apparatus, obtaining point cloud information by means of a structured light stripe, and further obtaining a three-dimensional model of the human face; and
    mapping the three-dimensional model onto a circular plane in an area-preserving manner so as to form a two-dimensional human face image,
    wherein the mapping of the three-dimensional model comprises:
    determining a boundary of a two-dimensional plane;

harmonically mapping the three-dimensional data to an interior of the boundary to form harmonic mapping points;

calculating second weights of the harmonic mapping points, and further calculating a weighted Voronoi diagram of the harmonic mapping points; and mapping the three-dimensional model onto the two-dimensional plane in the area-preserving manner according to the weighted Voronoi diagram.

12. A computer-readable storage medium having stored thereon computer-readable instructions which, when executed by one or more processors, implement a human face data processing method, the human face data processing method comprising:

acquiring a picture of a human face by means of a scanning apparatus, obtaining point cloud information by means of a structured light stripe, and further obtaining a three-dimensional model of the human face; and mapping the three-dimensional model onto a circular plane in an area-preserving manner so as to form a two-dimensional human face image, wherein the mapping of the three-dimensional model comprises:

determining a boundary of a two-dimensional plane;

harmonically mapping the three-dimensional data to an interior of the boundary to form harmonic mapping points;

calculating second weights of the harmonic mapping points, and further calculating a weighted Voronoi diagram of the harmonic mapping points; and mapping the three-dimensional model onto the two-dimensional plane in the area-preserving manner according to the weighted Voronoi diagram.

* * * * *